United States Patent [19]

Khera

[11] 4,039,302
[45] Aug. 2, 1977

[54] PROCESS AND CATALYST FOR SYNTHESIZING LOW BOILING (C1 TO C3) ALIPHATIC HYDROCARBONS FROM CARBON MONOXIDE AND HYDROGEN

[75] Inventor: Surjit Singh Khera, Upper Arlington, Ohio

[73] Assignee: Battelle Development Corporation, Columbus, Ohio

[21] Appl. No.: 646,566

[22] Filed: Jan. 5, 1976

[51] Int. Cl.$^2$ ............................ C10J 3/00; B01J 21/00; C07C 1/04
[52] U.S. Cl. .................................. 48/197 R; 252/465; 260/449.6 R; 260/449 M
[58] Field of Search ...................... 252/465; 260/449.6, 260/449 M; 48/197 R

[56] References Cited

U.S. PATENT DOCUMENTS

| | | | |
|---|---|---|---|
| 2,211,022 | 8/1940 | Michael et al. | 260/449 M |
| 2,231,990 | 2/1941 | Dreyfus | 260/449 M |
| 2,791,583 | 5/1957 | Weck | 260/449.6 X |
| 3,627,674 | 12/1971 | Nagl | 252/465 X |
| 3,872,180 | 3/1975 | Nakatomi et al. | 252/465 X |
| 3,928,000 | 12/1975 | Child et al. | 260/449 M |
| 3,928,238 | 12/1975 | Koberstein et al. | 252/465 |
| 3,931,052 | 1/1976 | Oleck et al. | 252/465 |

*Primary Examiner*—Patrick P. Garvin
*Assistant Examiner*—William G. Wright

*Attorney, Agent, or Firm*—Kenneth R. Warburton

[57] ABSTRACT

Low boiling ($C_1$ to $C_3$) aliphatic hydrocarbons are obtained by passing a mixture of hydrogen and carbon monoxide at a volume ratio of about 45:55 to 60:40 at a temperature between about 350° and about 500° C. and a pressure of about 200 p.s.i.g. to about 10,000 p.s.i.g. at a volumetric hourly space velocity of about 200 to about 6000 in contact with a catalyst comprising an interspersed mixture of cobalt oxide, aluminum oxide, zinc oxide and molybdenum oxide. The catalyst comprises about 0.2 to about 2.0 weight percent of cobalt oxide, about 55 to about 95 weight percent of aluminum oxide, about 5 to about 15 weight percent of zinc oxide and about 2 to about 20 weight percent of molybdenum oxide. In preparing the catalyst, the cobalt, aluminum and zinc can be precipitated separately as the corresponding carbonates or hydroxides and then admixed with ammonium paramolybdate prior to calcination or two or more of the metals such as cobalt, aluminum and zinc can be coprecipitated as the carbonates or hydroxides at a controlled pH with sodium carbonate or ammonium hydroxide from the corresponding aqueous nitrate or acetate solutions and thereafter admixed with ammonium paramolybdate and any remaining metal salt, such as, for example, cobaltous nitrate or zinc hydroxide. The admixed salts of cobalt, aluminum, zinc and molybdenum are then dried and calcined.

10 Claims, No Drawings

PROCESS AND CATALYST FOR SYNTHESIZING LOW BOILING (C1 TO C3) ALIPHATIC HYDROCARBONS FROM CARBON MONOXIDE AND HYDROGEN

This invention relates to a process for catalytically synthesizing low boiling ($C_1$ to $C_3$) aliphatic hydrocarbons from mixtures of carbon monoxide with hydrogen and to a catalyst for use in the synthesis of the low boiling aliphatic hydrocarbons.

BACKGROUND OF THE INVENTION

It is well known that there is an increasing shortage of natural gas (chiefly methane) in the United States and there is a generally limited supply of natural gas throughout the world. For this reason, attention is being directed to a substitute or supplement for natural gas. It is also well known that there is an increasing demand for other low boiling hydrocarbons for use as fuels themselves, for gas enrichment and for use in synthesizing certain organic compounds.

The synthesis of low boiling aliphatic hydrocarbons by hydrogenating carbon monoxide is not a new concept. In fact, the synthesis of methane by hydrogenating carbon monoxide was first described by P. Sabatier and J. B. Senderens in 1902 (Compt. Rend. 134, 514 and 689 [1902]). Higher boiling hydrocarbons were obtained from carbon monoxide and hydrogen in the early 1920's by F. Fischer and H. Tropsch (Chem. Ber. 56, 2428 [1923]). While, at the present time, processes are available for producing a full range of hydrocarbons by hydrogenating carbon monoxide, the economics of such processes has mitigated against their wide-spread commercialization. The products obtained in the catalytic hydrogenation of carbon monoxide can be one or more materials selected from hydrocarbons, alcohols, aldehydes, ketones, esters and fatty acids of almost any chain length, degree of saturation and structure. The relative extent to which one or more of these products is obtained can be controlled to some extent by the selection of the catalyst composition and operating conditions. Catalysts which heretofore have been of special interest in the synthesis of organic compounds from carbon monoxide and hydrogen are those wherein the metal component is selected from iron, cobalt, nickel, ruthenium, zinc and thorium. The behavior of these catalysts in hydrogenating carbon monoxide is dependent to a large extent upon the presence of chemical and structural promotors, upon the method used in preparing the catalyst, upon the catalyst surface conditions, upon the reaction conditions and upon the nature or make-up of the feed gas mixture, i.e., synthesis gas charged to the reaction system.

Nickel has been used as a catalyst for the synthesis of methane according to the reaction

$$CO + 3H_2 \rightleftarrows CH_4 + H_2O \qquad (1)$$

which proceeds from left to right at temperatures below about 500° C. and in the opposite direction at higher temperatures.

Cobalt admixed with thorium dioxide and magnesium oxide, as promotors, and kieselguhr, as a carrier, has been used as a catalyst for the synthesis of higher aliphatic hydrocarbons (F. Fischer and H. Tropsch, Brennstoff-Chem. 7, 97 [1926]; and F. Fischer and H. Pichler, Brennstoff-Chem. 20, 41, 221 and 247 [1939]).

Iron has been used as a catalyst for the synthesis of aliphatic and aromatic hydrocarbons. In the past, alkali has been used as a promotor when the catalyst contains iron. The alkali is reported to influence surface conditions of the catalyst and to enhance the production of higher molecular weight products. In the early work conducted by F. Fischer and H. Tropsch, alkali-promoted iron-copper catalysts were employed in producing high boiling (gasoline range) hydrocarbons. (F. Fischer and H. Tropsch, Brennstoff-Chem. 9, 21 [1928]). The promoting effect of alkali to iron catalysts was believed to be the result of the formation in its presence of ferric oxide ($Fe_2O_3$) and the prevention of its transistion to the less active magnetic iron oxide ($Fe_3O_4$). (G. LeClerc, Compt. Rend 207, 1099 [1939]).

In accordance with the present invention, the presence of alkali in the catalyst is kept at a minimum since it is believed that the presence of alkali in the catalyst of the invention causes the catalyst to fuse and thus materially decrease the surface available for catalytic purposes.

Sintered iron catalyst have previously been used in preparing branched-chain paraffins. These catalysts have been prepared by reducing precipitated iron-alumina catalysts at 1550° F. (British Pat. No. 473,932 [1937]; British Pat. No. 474,448 [1937]; and British Pat. No. 496,880 [1938]).

Ruthenium and ruthenium-containing catalysts have been used in the synthesis of high-melting waxes from hydrogen and carbon monoxide (H. Pichler, Brennstoff-Chem. 19, 226 [1938]; H. Pichler and H. Buffleb, Brennstoff-Chem. 21, 257, 273 and 285 [1940]). Other Group VIII metals, i.e., rhodium, palladium, osmium, iridium and platinum have been less satisfactory than ruthenium (U.S. Pat. No. 1,628,190 [1927]). The effect of pressure upon the yield and type of products with ruthenium catalysts is very pronounced.

Zinc oxide and mixtures of zinc oxide with chromic oxide have been used as catalysts for synthesizing methanol from hydrogen and carbon monoxide at temperatures above 300° C. and pressures above 200 atmospheres. (H. Pichler, Brennstoff-Chem. 33, 289 [1952]).

Oxide catalysts, in general, show a smaller degree of activity toward carbon monoxide plus hydrogen than the metal catalysts. On the other hand, metal catalysts, e.g., nickel, cobalt, iron and ruthenium, are more sensitive to sulfur and sulfur compounds than oxide catalysts.

Prior processes for hydrogenating carbon monoxide to methane and other low boiling hydrocarbons have required hydrogen to carbon monoxide ratios in the order of about 3:1 (see equation 1 hereinabove). Therefore, in many instances, it has been necessary to increase the hydrogen content of synthesis gas by the so-called water gas shift reaction, i.e.,

$$CO + H_2O \rightarrow CO_2 + H_2 \qquad (2)$$

The carbon dioxide formed in the water gas shift reaction is then removed by compressing the gas and scrubbing it with water or by reacting it with ethanolamines. The hydrogen thus obtained is used according to prior processes to increase the hydrogen to carbon monoxide ratio in synthesis gas to an amount of about 2:1 to 3:1, preferably the latter, i.e., about 3:1.

Coal has been used in the production of synthetic or substitute natural gas (SNG) comprising low boiling hydrocarbons according to the Lurgi process as described by Paul F. H. Rudolph in Chemical Age of India, 25, 289-299 (1974). In the Lurgi process for producing SNG from coal, five separate steps are required: (1) pressure gasification of coal to recover gaseous products and remove ash and tar; (2) crude gas shift conversion wherein steam is reacted with some carbon monoxide to form carbon dioxide and hydrogen, the latter being used to increase the hydrogen to carbon monoxide ratio in the synthesis gas; (3) Rectisol gas purification wherein organic solvents remove impurities from the gas; (4) methane synthesis where the carbon monoxide and hydrogen are reacted to produce methane; and (5) a Phenolsolvan process for treating the gas liquor from coal gasification to remove water-soluble components, e.g., phenols, ammonia and fatty acids.

In accordance with the present invention, a catalyst is provided for the hydrogenation of carbon monoxide to low boiling hydrocarbons wherein the $H_2$:CO ratio can be 1:1. Since this ratio is frequently obtained when coal is subjected to complete gasification, there is no need in the process of the present invention to employ a water gas shift reaction such as that used in the Lurgi process. While coal is an economical source of synthesis gas for use as feed gas in the process of the present invention, the synthesis gas can be obtained from any carbonaceous material which can be decomposed to hydrogen and carbon monoxide. Examples of such materials are fossil fuels such as natural gas, bituminous coal, lignite, oil shale, crude oil and residual fuel oils. For the most part, synthesis gas has been obtained from natural gas or coal. The theoretical ideal synthesis gas reaction may be represented as follows:

$$C + H_2O \rightarrow CO + H_2 \tag{3}$$

One of the impurities frequently present in synthesis gas obtained in the gasification of coal is sulfur or compounds of sulfur. As indicated hereinabove, metal catalysts such as nickel, cobalt, iron and ruthenium are poisoned by sulfur and sulfur compounds. Thus, synthesis gas containing sulfur or sulfur compounds has previously been subjected to a desulfurization process prior to being converted into hydrocarbons. One such process is the Girbitol process as described by C. B. Ames, Mines Magazine 32, 508 (1942). Other desulfurization processes include (1) the iron oxide process (C. C. Hall and A. R. Powell, Office of Technical Services Report No. PB288, Department of Commerce, Washington, D.C.); (2) the "Alkazid Process" (Lorenzen, Gerhard and Leithe, Gas and Wasserfach 86, 313 [1943]) in which an alkaline organic compound absorbs hydrogen sulfide and then is steam-stripped for reuse (H. A. Schade, E. Foran and R. C. Aldrich, Office of Technical Services Report No. PB373, Department of Commerce, Washington, D.C.); and (3) F. Fischer and H. Tropsch desulfurization by catalytic reduction of sulfur compounds to hydrogen sulfide (British Pat. No. 254,288 [1925]; British Pat. No. 282,634 [1926]; Canadian Pat. No. 266,382 [1926]; and German Pat. No. 558,558 [1926]).

A process for decomposing organic sulfur compounds to hydrogen sulfide by passing the gas at a temperature above 300° C. over a mixture of alkali metal carbonates and iron oxide is disclosed by Studien and Verwertungs G. m. b. H. in British Pat. No. 469,933 (1937) and German Pat. No. 651,462 (1937). In still another process I. G. Farbenindustrie A.-G. has disclosed a process for decomposing organic sulfur compounds to hydrogen sulfide simultaneously with the water gas shift reaction (U.S. Pat. No. 1,695,130 [1928]).

SUMMARY OF THE INVENTION

In accordance with the present invention, a catalyst is provided which is resistant to poisoning by sulfur or compounds of sulfur present in products of coal gasification. Thus, the present invention does not require total desulfurization of the synthesis gas obtained in coal gasification prior to being catalytically converted to low boiling hydrocarbons.

The products with which the present invention is concerned are the $C_1$ to $C_3$ aliphatic hydrocarbons. In some instances, a very minor, yet detectable, amount of butane may be present. The $C_1$ to $C_3$ aliphatic hydrocarbons are desirable fuel gases, per se, or they may be used for gas enrichment. They also may be separated into their individual constituents and used as intermediates in forming other organic compounds. Methane is widely used to upgrade manufactured gas. Ethane can be used in the production of ethylene. It is useful also in the production of acetic acid, acetaldehyde, ethyl chloride and nitroethane. Propane is widely used as a fuel in liquified petroleum gas (LPG). It is used also as a refrigerant in chemical, petroleum refining and gas process operations. Still further, it is useful as a solvent and for injection into subterranean formations to increase the production of crude oil from wells.

Essentially, the present invention comprises a process for synthesizing low boiling aliphatic hydrocarbons from carbon monoxide and hydrogen. The process utilizes a novel catalyst comprising an interspersed mixture of cobalt oxide, aluminum oxide, zinc oxide and molybdenum oxide. According to the process, a synthesis gas comprising a mixture of hydrogen and carbon monoxide having a volume ratio of about 45:55 to 60:40, preferably a molar ratio of 1:1, is passed through a reaction zone at a temperature of about 350° to about 500° C. and a pressure of about 200 p.s.i.g. to about 10,000 p.s.i.g. or higher, e.g., 25,000 p.s.i.g., at a space velocity (volume of gas per hour per volume of catalyst) of about 200 to about 6000 in contact with a catalyst comprising an interspersed mixture of cobalt oxide, aluminum oxide, zinc oxide and molybdenum oxide. A gaseous mixture comprising a mixture of low boiling aliphatic hydrocarbons is recovered from the reaction product. The preferred temperature range is about 375° to about 450° C.; the preferred pressure range is about 200 to about 3000 p.s.i.g.; and the preferred space velocity is about 900 to about 2000. Optimum values of temperature and pressure may vary according to the composition of the feed gas, type and amount of catalyst, throughput velocity and the like.

DETAILED DESCRIPTION OF THE INVENTION

The feed gas (synthesis gas) employed in the process of the invention may be obtained from a variety of carbonaceous materials. From an economic standpoint, it is preferred to use a low cost material such as bituminous coal, lignite, oil shale and low grade crude and residual fuel oils. Since sulfur is undesirable in pipeline gas, it is preferred to use a synthesis gas source material which contains little or no sulfur when preparing a pipeline gas. While sulfur can be removed from the pipeline gas prior to distribution, the purification step adds to the overall cost and may offset the advantage of using a low cost material in the first instance. The removal of sulfur, however, is not necessary insofar as the catalyst of the invention is concerned since the catalyst is resistant to sulfur. The synthesis gas is advantageously obtained by gasification of a low cost coal with steam. As indicated above, however, the process of the invention is not limited to the use of synthesis gas derived from coal but is applicable to mixtures of hydrogen and carbon monoxide, with or without other gaseous ingredients from any source. The presence of carbon dioxide in the synthesis gas has no deleterious affect on methanation. For methanation, the synthesis gas should contain hydrogen and carbon monoxide in a volume ratio of 45:55 to 60:40, preferably a molar ratio of 1:1 since the primary reaction is $$2CO + 2H_2 \rightarrow CH_4 + CO_2 \quad (4)$$

The carbon dioxide obtained according to the equation (4) is advantageously recycled to a gasifier to obtain improved carbon utilization. There is no water or, if any, only small amounts of water formed when a catalyst of the invention is used in the process of the invention to produce low boiling aliphatic hydrocarbons.

The catalyst of the present invention comprises an interspaced mixture of cobalt oxide, aluminum oxide, zinc oxide and molybdenum oxide, which mixture, by elemental analysis, contains less than about 2.0 weight percent, preferably less than about 0.1 weight percent of alkali metal. While it is preferred to avoid the use of alkali metals in forming the oxides of cobalt, aluminum, zinc and molybdenum because of the difficulty in producing a catalyst which, by elemental analysis, contains less than about 2.0 weight percent of alkali metal, an alkali metal compound such as, for example, sodium carbonate can be used if, the pH is controlled and kept below 7 and the precipitate is washed, to produce a catalyst which, by elemental analysis, contains less than about 2.0 weight percent of the alkali metal. To avoid the difficulty of removing an alkali metal from the catalyst, it is preferred to employ a non-alkali metal electrolyte, such as, for example, ammonium hydroxide, in the formation of the catalyst of the present invention. Even when using ammonium hydroxide, a small amount, usually less than about 0.1 percent, of alkali metal may appear in the catalyst as a result of impurities in some of the starting materials. The proportion of cobalt oxide in the catalyst comprises about 0.2 to about 2.0 weight percent of the catalyst, preferably about 0.4 to about 1.0 weight percent. The proportion of aluminum oxide in the catalyst comprises about 55 to about 95 weight percent of the catalyst, preferably about 65 to about 90 weight percent. The proportion of zinc oxide in the catalyst comprises about 5 to about 15 weight percent of the catalyst, preferably about 7 to about 10 weight percent. The proportion of molybdenum oxide in the catalyst comprises about 2 to about 20 weight percent of the catalyst, preferably about 3 to about 16 weight percent.

The employed catalyst, i.e., dried and/or calcined, as well as that optionally subjected to a reduction step prior to usage, is an interspaced mixture of the oxides of cobalt, aluminum, zinc and molybdenum in the foregoing proportions. For teaching the invention, the oxides of cobalt and molybdenum in this interspaced mixture also are referred to as "cobalt oxide" and "molybdenum oxide", respectively. By "cobalt oxide" there is intended to mean each of and any mixture of cobaltous oxide (CoO), cobaltic oxide ($Co_2O_3$) and cobalto-cobaltic oxide ($Co_3O_4$) also sometimes called cobaltosic oxide. By "molybdenum oxide" there is intended to mean each of and any mixture of molybdenum sesquioxide ($Mo_2O_3$), molybdenum dioxide ($MoO_2$), molybdenum trioxide ($MoO_3$) and molybdenum pentoxide ($Mo_2O_5$). The extent to which any one or more of the oxides of cobalt and molybdenum are present in the employed catalytic interspersed mixture depends upon the specific drying, calcination and reduction treatments and conditions to which the precipitated hydroxides or carbonates are subjected prior to usage as employed catalyst.

Even though each of the constituents in the catalyst of the present invention has been used in prior catalysts for hydrogenating carbon monoxide, I know of no catalyst consisting of a combination consisting of an interspaced mixture of cobalt oxide, aluminum oxide, zinc oxide and molybdenum oxide which is used in synthesizing a low boiling mixture of $C_1$ to $C_3$ hydrocarbons.

The catalyst of the invention can be prepared by any of several methods so long as, by elemental analysis, it contains less than about 2.0 weight percent of alkali metal, preferably less than about 0.5 weight percent and most preferably less than 0.1 weight percent of alkali metal. The oxides of cobalt, aluminum, zinc and molybdenum can be prepared separately and then admixed with each other, or any two or more of these metal oxides can be formed in the presence of each other and then admixed with any remaining oxide or oxides. In order to prepare an interspersed mixture of the oxides, it is preferred to prepare the oxides of the metals selected from cobalt, aluminum, zinc and molybdenum in the presence of each other. Likewise, the compounds from which the oxides of cobalt, aluminum, zinc and molybdenum are prepared separately and then admixed with each other prior to calcination or any two or more of the compounds from which the oxides are prepared can be prepared in the presence of each other and then admixed with any remaining compound selected from cobalt, aluminum, zinc and molybdenum. The mixture thus obtained is dried and calcined to form an interspaced mixture of the oxides of cobalt, aluminum, zinc and molybdenum. The compounds from which the oxides are prepared can be hydroxides, nitrates, carbonates or ammonium salts or a mixture of two or more of the hydroxides, nitrates, carbonates and ammonium salts. The compounds from which the oxides are prepared can be admixed, dried and calcined to form an interspersed mixture of the oxides of cobalt, aluminum, zinc and molybdenum. Alternatively, the compounds from which the oxides are prepared can be dried, then admixed and calcined. A further modification comprises drying the precursor of the oxides, followed by calcining and then admixing the calcined products. More specifically, the catalyst of the invention can be prepared by precipitating one or more of the metals selected from cobalt, aluminum and zinc from aqueous solutions thereof with sodium carbonate or with a non-alkali metal electrolyte, such as, for example, ammonium hydroxide. The precipitated metal compounds thus formed are then admixed with ammonium paramolybdate, dried and calcined.

In one embodiment of the invention, the carbonates of cobalt, aluminum and zinc are coprecipitated with sodium carbonate from an aqueous mixture of the corresponding nitrates at a pH of 6.2. The mixture of carbonates thus formed is admixed with an aqueous solution of ammonium paramolybdate, dried and calcined to form an interspersed mixture of the oxides of cobalt, aluminum, zinc and molybdenum.

In another embodiment of the invention, the carbonates of aluminum and zinc are coprecipitated with sodium carbonate from an aqueous mixture of the corresponding nitrates at a pH of 5.5 which is then adjusted to a pH of 8.0 with ammonium hydroxide. The mixture of carbonates thus formed is admixed with a precipitate which is formed by combining an aqueous solution of cobaltous nitrate and an aqueous solution of ammonium paramolybdate which has been neutralized (pH of 6.8) with ammonium hydroxide. The mixture of aluminum carbonate, zinc carbonate, cobaltous nitrate and ammonium paramolybdate is then dried and calcined to form an interspersed mixture of the oxides of cobalt, aluminum, zinc and molybdenum.

In a further embodiment of the invention, zinc hydroxide is precipitated with ammonium hydroxide from an aqueous solution of zinc nitrate at a pH of 6.5. Aluminum hydroxide is precipitated with ammonium hydroxide from an aqueous solution of aluminum nitrate at a pH of 6.8. The hydroxides of zinc and aluminum thus formed are then mixed together. The mixture of aluminum and zinc hydroxides is then admixed with a precipitate which is formed by combining an aqueous solution of cobaltous nitrate and an aqueous solution of ammonium paramolybdate which has been neutralized (pH of 6.8) with ammonium hydroxide. The mixture of aluminum hydroxide, zinc hydroxide, cobaltous nitrate and ammonium paramolybdate is then dried and calcined to form an interspersed mixture of the oxides of cobalt, aluminum, zinc and molybdenum.

In still a further embodiment of the invention, aluminum hydroxide and cobaltous hydroxide are coprecipitated with ammonium hydroxide from an aqueous mixture of the corresponding nitrates at a pH of 6.0. Zinc hydroxide is then precipitated with ammonium hydroxide from an aqueous solution of zinc nitrate at a pH of 7.0. The hydroxides of cobalt, aluminum and zinc thus formed are then admixed with an aqueous solution of ammonium paramolybdate. The mixture is then dried and calcined to form an interspersed mixture of the oxides of cobalt, aluminum, zinc and molybdenum.

In a further embodiment of the invention, zinc carbonate is precipitated with sodium carbonate from an aqueous solution of zinc nitrate at a pH of 8.0. Aluminum hydroxide is precipitated with ammonium hydroxide from an aqueous solution of aluminum nitrate at a pH of 6.5. The zinc carbonate and aluminum hydroxide are then admixed with a precipitate which is formed by combining an aqueous solution of cobaltous nitrate and an aqueous solution of ammonium paramolybdate which has been neutralized (pH of 6.8) with ammonium hydroxide. The mixture of zinc carbonate, aluminum hydroxide, cobaltous nitrate and ammonium paramolybdate is then dried and calcined to form an interspersed mixture of the oxides of cobalt, aluminum, zinc and molybdenum.

Catalyst preparation is conducted under controlled conditions: generally a temperature of about 20° to about 95° C.; a maintaining of the pH of the solution at a value within the range of about 5.5 to about 9.5, preferably within the range of about 6.0 to about 7.5 depending upon the particular materials involved; when coprecipitating the carbonates of cobalt, aluminum and zinc from the corresponding nitrates with sodium carbonate, a pH of 6.2 has given good results; when coprecipitating the carbonates of aluminum and zinc, an initial pH of 5.5 adjusted to a pH of 8.0 with ammonium hydroxide has given good results; when separately precipitating cobaltous hydroxide with ammonium hydroxide from cobaltous nitrate, a higher pH in the order of about 8.5 to 9.5 has given a good catalyst when subsequently admixed with other hydroxides of aluminum and zinc and then dried and calcined; when separately precipitating the hydroxides of aluminum and zinc from the corresponding nitrates, good results have been obtained at a pH of 6.5 for zinc hydroxide and a pH of 6.8 for aluminum hydroxide; when coprecipitating the hydroxides of cobalt and aluminum from the corresponding nitrates, a pH of 6.0 has given good results; when separately precipitating the carbonate of zinc from zinc nitrate with sodium carbonate, a pH of 8.0 has given good results; and in forming a precipitate between cobaltous nitrate and ammonium paramolybdate, a pH of 6.8 has resulted in the formation of an effective catalyst upon subsequent calcination.

If the pH is not maintained during the preparation of the catalyst as taught hereinabove, the resulting catalyst is less effective in the formation of low boiling ($C_1$ to $C_3$) aliphatic hydrocarbons. To achieve this pH control, it may be necessary to add ammonia, ammonium hydroxide or similar substance, but not alkali, into the solution (suspension). Alkali is undesirable since it tends to lower the fusion temperature of the catalyst and also promotes the formation of a liquid hydrocarbon fraction. Thus, it is preferred to employ an alkali-free catalyst or a catalyst which, by elemental analysis, contains less than about 0.5 weight percent of an alkali metal, in the process of the invention to produce low boiling $C_1$ to $C_3$ aliphatic hydrocarbons. The pH is kept at a constant value, preferably through control by a pH meter. In preferred embodiments of the invention, cobalt, aluminum and zinc are precipitated separately as their hydroxides, preferably with ammonium hydroxide under controlled temperature conditions within the range of about 20° to about 95° C., i.e., about 90° to 95° C. for cobaltous hydroxide and about 20° to 30° C. for aluminum hydroxide and zinc hydroxide, while maintaining the pH of the solutions at a value within the range of about 6 to about 9.5, i.e., pH's of 6 to 7.5 for aluminum hydroxide and zinc hydroxide and a pH of 8.5 to 9.5 for cobaltous hydroxide. The cobalt, aluminum and zinc hydroxides are then admixed with each other. The mixture of cobalt, aluminum and zinc hydroxides is then admixed with an aqueous solution of ammonium paramolybdate and heated at 70° C. for 2 hours. The mixture is then dried and calcined in the presence of air or oxygen.

Drying may be effected under relatively mild conditions, e.g., 8 to 12 hours at 100° to 120° C. Drying can amount to calcination so long as precipitated hydroxides convert to their oxides and the dried mixture is friable. Alternatively to such concurrent drying and calcination, one may calcinate, after drying, at higher temperatures, for example, at 300° to 400° C. for 2 to 12 hours to obtain a calcinated catalyst in the form of interspersed mixed oxides, the higher temperature normally being associated with the shorter time and vice versa.

The dried catalyst, in which the mixed oxides are interspersed, optionally can be subjected to a reducing step prior to use. Such reduction step can amount to calcination. Reduction can be effected by heating the catalyst composition in the presence of hydrogen at an elevated temperature, normally at a temperature of about 300° to 450° C. The hydrogen treatment or preactivation may change the oxidation state of the metals present or it may reduce at least a portion of the oxides to lower oxides and/or to their metallic state. Depending upon the degree of reduction, a dried or dried and calcined catalyst may be treated with hydrogen at a temperature of about 300° to about 450° C. for a period of 5 minutes to 48 hours, the longer time normally being associated with the lower temperature. The catalyst may be formed into any desired shape such as, for example, granules, pills, pellets and the like. Depending upon the catalyst composition, the ratio of hydrogen to carbon monoxide in the synthesis gas and the operating variables, such as, time, temperature, pressure and space velocity, treatment of the catalyst with hydrogen may or may not improve its effectiveness in the conversion of synthesis gas to low boiling ($C_1$ to $C_3$) aliphatic hydrocarbons. For this reason, reduction of the catalyst prior to use in the process of the invention is considered to be an optional step in the process.

The use of a catalyst of the invention is particularly effective in the synthesis of low boiling aliphatic hydrocarbons from mixtures of hydrogen and carbon monoxide obtained in the gasification of coal in the presence of sulfur compounds, such as hydrogen sulfide and mercaptans, since the catalyst is resistant to sulfur poisoning. By contrast, conventional iron and nickel catalysts are rapidly poisoned by the presence of sulfur compounds necessitating extensive gas purification facilities to maintain catalyst activity. These facilities may not be required when a catalyst of the invention is employed. Thus there will be savings in the capital and operating cost for the process.

In accordance with the present invention, coal or similar carbonaceous material may be gasified at elevated temperatures of about 800° C. by reaction with oxygen/steam at about 1000 to 3000 p.s.i.g. or the product gas from a low pressure gasifier be compressed down stream. Carbon dioxide may be recycled to the gasifier so that the product gas from the gasifier has a carbon monoxide to hydrogen ratio as required by this invention which may also be achieved by operating the gasifier at still elevated temperatures at about 1200° C. and adjusting the oxygen/steam ratio to the gasifier.

The process of the invention can be operated as a multistage or single stage process in either a fixed-bed or moving-bed reactor. Preferably, however, a recycle system, in which unconverted hydrogen and carbon monoxide are recycled to the reactor, is used. In any process according to the invention, temperature and pressure control in or between synthesis converters can be any suitable means such as, for example, feed gas preheaters, coolers, quenchers, compressors and the like.

The reaction of hydrogen with carbon monoxide in volume ratios of 45:55 to 60:40 and preferably a molar ratio of about 1:1 to produce low boiling ($C_1$ to $C_3$) aliphatic hydrocarbons is conducted at a temperature of about 350° to about 500° C., preferably about 375° to about 425° C., a space velocity (volume of gas per hour per volume of catalyst) of about 200 to about 6000, preferably about 900 to about 2000, and a pressure of about 200 to about 10,000 p.s.i.g., preferably about 200 to about 3000 p.s.i.g., in the presence of an interspersed mixture of the oxides of cobalt, aluminum, zinc and molybdenum which mixture, by elemental analysis, contains an alkali metal content of less than 2.0 percent, based on the weight of the catalyst, and preferably less than 0.5 weight percent and most preferably less than 0.1 weight percent. The space velocity will depend to some extent upon the type of reaction system used. For fixed-bed reactors, the number of volumes of gas per volume of catalyst per hour, can be about 200 to about 6000 and is preferably about 900 to about 2000; for fluidized-bed operation using recycle, the total feed space velocity is much higher and may be about 3000 to about 5000.

The invention is further illustrated by reference to the following examples which are intended to be representative rather than restrictive of the scope of the invention.

EXAMPLE 1

PREPARATION OF CATALYST

In this example, the carbonates of cobalt, aluminum and zinc are coprecipitated and then admixed with ammonium paramolybdate prior to drying according to the procedure which follows.

An aqueous solution of zinc nitrate, cobaltous nitrate and aluminum nitrate is prepared by dissolving 8.4 gms of zinc nitrate, 0.38 gm of cobaltous nitrate and 158.6 gms of aluminum nitrate in 1500 ml of distilled and deionized water in a 4000 ml beaker (I). The solution thus formed is stirred and heated to 90° to 95° C. In a separate 3000 ml beaker (II) containing 1500 ml of distilled water is placed 70 gms of anhydrous sodium carbonate. The solution of sodium carbonate is stirred and heated to 90° to 95° C. When the solutions in beakers (I) and (II) are at 90° to 95° C., the sodium carbonate solution in beaker (II) is added quickly to the solution in beaker (I) with constant stirring. When the solutions are mixed, there is a rapid evolution of gas. The pH of the solution at this point is 6.2. The precipitate thus formed comprising the carbonates of cobalt, aluminum and zinc is separated from the reaction mass by filtration. The precipitate is then washed with two 300 ml portions of distilled water. The washed precipitate is then admixed with 500 ml of distilled water and 1.31 gms of ammonium paramolybdate in a 1000 ml beaker (III). The mixture in beaker (III) is then placed in an oven at 110° C. for 12 hours or more until the mixture is dry. The dried mixture is then calcined by passing air over the mixture at 300° C. for 12 hours. The catalyst thus obtained comprises an interspersed mixture of the oxides of cobalt, aluminum, zinc and molybdenum in the following weight proportions.

| Composition | Weight Percent |
| --- | --- |
| Cobalt oxide | 0.8 |
| Aluminum oxide | 86.2 |
| Zinc oxide | 9.2 |
| Molybdenum oxide | 3.8 |

The alkali metal content, by elemental analysis, is less than 2 weight percent of the mixture.

TEST OF THE CATALYST

The catalyst obtained above is evaluated in the synthesis of low boiling aliphatic hydrocarbons from a mixture of hydrogen and carbon monoxide in two fixed-bed reactors connected in series. In evaluating the catalyst, it is sized by screening through sieves. The catalyst particles which are used are those which pass through a U.S. Mesh No. 12 sieve and are retained on a U.S. Mesh No. 30 sieve.

Each reactor consists of a 304 stainless steel tube 18 inches in length with an inside diameter of ¾ inch and an outside diameter of 3 inches. A constant temperature zone in the reactor has a volume of 25cc. The gas inlet side of the first tube is connected to a high pressure rotameter, a flow control needle valve and a pressure regulator. The outlet side of the first tube is connected to the inlet side of the second tube. The outlet side of the second tube is connected to a pressure condenser surrounded by ice, a flow control needle valve, a dry ice trap and flow indicators. Product samples for analysis can be withdrawn from the outlet tube of each reactor.

The synthesis gas used in the evaluation of the catalyst consists of a mixture of hydrogen and carbon monoxide in a volume ratio of 50:50 (molar ratio of hydrogen to carbon monoxide of 1:1).

In evaluating the catalyst, the first reactor is charged with 10 gms (11 cc) of the sieved catalyst. The second reactor is charged with 10 gms (12cc) of the sieved catalyst. In each instance, the catalyst is maintained in place by packing each end of the reactor with ⅛ inch fish spline insulators. In starting the test, the synthesis gas at 1000 p.s.i.g. is passed through the system and the flow is stabilized at 18 liters per hour at room conditions. When it is certain that there are no leaks in the system, the heaters for the reactors are turned on. The temperature in the first reactor is increased to 350° C. while the temperature in the second reactor is increased to 400° C. The reaction system is maintained at these temperatures and a pressure of 1000 p.s.i.g. over a period of 6 hours. Gas samples are obtained from the second reactor and analyzed by a 2002 Varian Gas Chromatography Unit. At the end of the evaluation, the catalyst is cooled to room temperature and weighed. An observation is made as to whether any liquids are found in the traps. In using the catalyst of Example 1, the atomic ratio for $C_2-C_3/C_1$ in the product is 0.22. The conversion of carbon monoxide is 15.1 percent.

When this test is carried out at 450° C. for 2 hours, the conversion of carbon monoxide is increased to 51.1 percent. There is also an increased yield of methane (17.6 volume percent) and ethane-propane (2.4 volume percent).

When this test is carried out at 475° C for 1 hour, the conversion of carbon monoxide is further increased to 58.6 percent. The higher temperature also results in further increases in methane (24.2 volume percent) and ethane-propane (3.0 volume percent).

The data obtained in the evaluation of the catalyst of Example 1 are summarized in Table 1.

EXAMPLE 2

PREPARATION OF CATALYST AND TEST OF THE CATALYST

The catalyst in this example is the same as that in Example 1. The test procedure also corresponds to that used in Example 1. In this example, however, the catalyst, prior to evaluation in the synthesis of low boiling hydrocarbons from a mixture of hydrogen and carbon monoxide is treated with hydrogen. Thus, prior to introduction of synthesis gas, the catalyst is heated in a stream of hydrogen (6ml/sec) at atmospheric pressure for 48 hours. The temperature is increased slowly to 400° C. over a period of 8 hours. The temperature is then further increased to 450° C. where it is maintained for 40 hours. The catalyst is then allowed to cool in the hydrogen stream. Two reactors are used in series; each reactor contains 10 gms of the reduced catalyst. The synthesis gas, as in Example 1, comprises a mixture of hydrogen and carbon monoxide in a volume ratio of 50:50 (molar ratio of hydrogen to carbon monoxide of 1:1).

In this evaluation, the temperature of the first reactor and second reactor is maintained, respectively, at 350° and 400° C. for 4 hours. Thereafter, both of the reactors are maintained at 450° C. for 1 hour. Gas samples from the second reactor are analyzed by a 2002 Varian Gas Chromatography Unit. The data obtained in the evaluation of the hydrogen-reduced catalyst are summarized in Table 1.

EXAMPLE 3

PREPARATION OF CATALYST

In this example, the carbonates of aluminum and zinc are coprecipitated and then admixed with the precipitate formed from an admixture of cobaltous nitrate and ammonium paramolybdate prior to drying according to the procedure which follows.

An aqueous solution of zinc nitrate and aluminum nitrate is prepared by dissolving 8.4 gms of zinc nitrate and 158.6 gms of aluminum nitrate in 1500 ml of distilled and deionized water in a 4000 ml beaker (I). The solution thus formed is stirred and heated to 90° to 95° C. In a separate 3000 ml beaker (II) containing 1500 ml of distilled water is placed 66.5 gms of anhydrous sodium carbonate. The solution of sodium carbonate is stirred and heated to 90° to 95° C. When the solutions in beakers (I) and (II) are at 90° to 95° C., the sodium carbonate solution in beaker (II) is added to beaker (I) with constant stirring. The pH of the solution thus obtained is 5.5. Ammonium hydroxide is then added to the solution to obtain a pH of 8. The precipitate thus obtained is separated from the reaction mass by filtration. The precipitate is then washed with two 300 ml portions of distilled water. The washed precipitate is then transferred to a 1000 ml beaker (III) for subsequent admixture with the combined precipitate of cobalt and molybdenum obtained as hereinafter described.

An aqueous solution of cobaltous nitrate is prepared by dissolving 0.38 gm of cobaltous nitrate in 10 ml of distilled water in a 100 ml beaker. (IV).

In a separate 100 ml beaker (V) containing 10 ml of distilled water is dissolved 1.31 gms of ammonium paramolybdate. The ammonium paramolybdate solution in beaker (V) is then neutralized (pH of 6.8) with ammonium hydroxide after which it is admixed with the cobalt nitrate solution in beaker (IV). A thick, blue colored combined precipitate of cobalt and molybdenum is obtained. The precipitate is separated from the reaction mass by filtration and washed with 100 ml of distilled water. The combined precipitate of cobalt and molybdenum is added to precipitates of zinc and aluminum in beaker (III). The mixture of precipitates of cobalt, molybdenum, zinc and aluminum is then admixed with 300 ml of distilled water after which the mixture is dried in an oven at 120° C. for 12 hours. The dried mixture is then calcined by passing air over the mixture at 400° C. for 12 hours. The catalyst thus obtained comprises an interspersed mixture of the oxides of cobalt, aluminum, zinc and molybdenum in the following weight proportions.

| Composition | Weight Percent |
|---|---|
| Cobalt oxide | 0.8 |
| Aluminum oxide | 86.2 |
| Zinc oxide | 9.2 |
| Molybdenum oxide | 3.8 |

The alkali metal content, by elemental analysis, is less than 2.0 weight percent of the mixture.

TEST OF THE CATALYST

The reaction system used to evaluate the catalyst is the same as that described in Example 1, i.e., two reactors connected in series, each reactor containing 10gms (13 cc) of catalyst. In this Example 3, however, the catalyst is reduced with hydrogen before starting the evaluation. Thus, prior to the introduction of synthesis gas into the system, hydrogen at 1000 p.s.i.g. is introduced for 1 hour into the first reactor at 350° C. and the second reactor at 400° C. Thereafter, synthesis gas comprising a mixture of hydrogen and carbon monoxide in a volume ratio of 52.5:47.5 (molar ratio of hydrogen to carbon monoxide of about 52.5:47.5) is introduced into the system. The catalyst in the first reactor is maintained at 350° C. for 4 hours. The catalyst in the second reactor is maintained at 400° C. for 4 hours. Thereafter, each reactor is maintained at 450° C. for 2 hours.

The data obtained in the evaluation of the catalyst of Example 3 are summarized in Table 1.

EXAMPLE 4

PREPARATION OF CATALYST

In this example, the catalyst is prepared by the same procedure and when using the same weights of materials as in Example 3. The catalyst comprises an interspersed mixture of the oxides of cobalt, aluminum, zinc and molybdenum in the following weight proportions.

| Composition | Weight Percent |
| --- | --- |
| Cobalt oxide | 0.8 |
| Aluminum oxide | 86.2 |
| Zinc oxide | 9.2 |
| Molybdenum oxide | 3.8 |

The alkali metal content, by elemental analysis, is less than 2.0 weight percent of the mixture.

TEST OF THE CATALYST

The reaction system used to evaluate the catalyst is the same as that described in Example 1, i.e., two reactors connected in series. In this Example 4, the catalyst is reduced with hydrogen before starting the evaluation, as in Example 3, by passing hydrogen through the system at 1000 p.s.i.g. at a flow rate of 18 liters per hour for 1 hour. The first reactor is maintained at 350° C. while the second reactor is maintained at 400° C. At the completion of 1 hour, the hydrogen flow is discontinued. Then, synthesis gas comprising a mixture of hydrogen and carbon monoxide in a volume ratio of 50:50 (molar ratio of hydrogen to carbon monoxide of 1:1), is passed through the reaction system, the first reactor being maintained at 350° C., the second reactor being maintained at 450° C.

The evaluation is then repeated with each reactor at 450° C.

The data obtained in the evaluation of the catalyst at 350°/450° C. and 450°/450° C. in this Example 4 are summarized in Table 1.

Table 1

| Ex. No. | Catalyst Composition * | | Catalyst Reduction hr/° C. | Reactor Temp. ° C. | S.V. $hr^{-1}$ | CO Conversion % | Final Gas : Vol.% | | | | | | Liquids Water ** | $C_2$-$C_3$ $C_1$ | Methane Vol.% *** | $C_2$-$C_3$ Vol.% **** |
| --- | --- | --- | --- | --- | --- | --- | --- | --- | --- | --- | --- | --- | --- | --- | --- | --- |
| | | | | | | | $C_1$ | $C_2$ | $C_3$ | $CO_2$ | $H_2$ | CO | | | | |
| 1 | CoO | 0.8 | None | 350/400 | 783 | 15.1 | 4.5 | 0.5 | — | 2.5 | 47.5 | 45.0 | t | 0.22 | 4.6 | 0.5 |
| | $Al_2O_3$ | 86.2 | None | 450 | 783 | 51.1 | 15.0 | 2.0 | — | 15.0 | 35.5 | 32.5 | t | 0.27 | 17.6 | 2.4 |
| | ZnO | 9.2 | None | 475 | 783 | 58.6 | 20.0 | 2.5 | — | 17.5 | 30.0 | 30.0 | t | 0.25 | 24.2 | 3.0 |
| | $MoO_2$ | 3.8 | | | | | | | | | | | | | | |
| 2 | CoO | 0.8 | 48/450 | 350/400 | 1800 | 16.1 | 5.0 | 0.5 | t | 3.75 | 38.3 | 52.5 | — | 0.25 | 5.2 | 0.5 |
| | $Al_2O_3$ | 86.2 | 48/450 | 450/450 | 1800 | 36.0 | 12.0 | 1.75 | — | 11.25 | 27.5 | 47.5 | — | 0.29 | 13.5 | 2.0 |
| | ZnO | 9.2 | | | | | | | | | | | | | | |
| | $MoO_2$ | 3.3 | | | | | | | | | | | | | | |
| 3 | CoO | 0.8 | 1 | | | | | | | | | | | | | |
| | $Al_2O_3$ | 86.2 | 350/400 | 350/400 | 692 | 23.6 | 5.0 | — | — | 6.25 | 52.5 | 36.25 | — | 0 | 7.8 | 0 |
| | ZnO | 9.2 | 1 | | | | | | | | | | | | | |
| | $MoO_2$ | 3.8 | 350/400 | 450/450 | 692 | 42.5 | 12.5 | 1.0 | 0.25 | 12.5 | 36.3 | 37.5 | — | 0.22 | 14.3 | 1.4 |
| | CoO | 0.8 | 1 | | | | | | | | | | | | | |
| 4 | $Al_2O_3$ | 86.2 | 350/400 | 350/450 | 900 | 0 | 0 | — | — | t | 55.0 | 45.0 | — | — | 0 | 0 |
| | ZnO | 9.2 | 1 | | | | | | | | | | | | | |
| | $MoO_2$ | 3.8 | 350/400 | 450/450 | 900 | 16.2 | 3.75 | t | — | 5.0 | 45.0 | 46.25 | — | 0.05 | 3.9 | 0 |

*Cobalt oxide is presented as cobaltous oxide (CoO) for convenience in providing weight percent values.
Molybdenum oxide is presented as molybdenum dioxide ($MoO_2$) for convenience in providing weight percent values.
**t = trace, <1 ml water per 4 cu. ft. of feed gas.
***volume percent methane in final gas on a carbon dioxide-free basis.
****Volume percent $C_2C_3$ in final gas on a carbon dioxide-free basis.

All of the examples listed in Table 1 report the results obtained when evaluating a catalyst wherein sodium carbonate is used to precipitate two or more of the metal oxide precursors. It will be noted from the data in Table 1 that higher reactor temperatures favor the formation of greater yields of the low boiling ($C_1$ to $C_3$) aliphatic hydrocarbons. It will be noted further that lower space velocities, in general, result in higher conversions. The catalyst which has been reduced with hydrogen does not substantially improve the conversion of hydrogen and carbon monoxide to low boiling aliphatic hydrocarbons under the specific conditions of the synthesis reaction.

EXAMPLE 5

PREPARATION OF CATALYST

In this example, the hydroxides of aluminum and zinc are precipitated separately and then admixed with the precipitate formed from an admixture of cobaltous nitrate and ammonium paramolybdate prior to drying according to the procedure which follows.

An aqueous solution of zinc nitrate is prepared by dissolving 8.4 gms of zinc nitrate in 200 ml of distilled water in a 500 ml beaker. Ammonium hydroxide is added slowly to the aqueous solution of zinc nitrate at 70° C. until the pH of the solution is 6.5. The precipitate thus formed comprising zinc hydroxide is separated from the reaction mass by filtration, washed with 100 ml of distilled water and transformed to a 500 ml beaker (I).

An aqueous solution of aluminum nitrate is prepared by dissolving 158.6 gms of aluminum nitrate in 1000 ml of distilled water in a 4000 ml beaker. Ammonium hydroxide is added slowly to the aqueous solution of aluminum nitrate at room temperature until the pH of the solution is 6.8. In this disclosure, including the examples, there is intended by "room temperature" to mean a temperature of 20° to 25° C. (about 68° to 77° F.). The precipitate thus formed comprising aluminum hydroxide is separated from the reaction mass by filtration, washed twice with 600 ml portions of distilled water and then admixed with the zinc hydroxide in beaker (I).

An aqueous solution of cobaltous nitrate is prepared by dissolving 0.38 gm of cobaltous nitrate in 10 ml of distilled water in a 100 ml beaker.

An aqueous solution of ammonium paramolybdate is prepared by dissolving 1.31 gms of ammonium paramolybdate in 10 ml of distilled water in a 100 ml beaker. The pH of the solution is adjusted to 6.8 with ammonium hydroxide.

The aqueous solutions of cobaltous nitrate and ammonium paramolybdate are admixed whereupon a thick, blue colored combined precipitate of cobalt and molybdenum is obtained. The precipitate is separated from the reaction mass by filtration and washed with 100 ml of distilled water. The combined precipitate of cobalt and molybdenum is added to the precipitates of zinc hydroxide and aluminum hydroxide in in beaker (I). To beaker (I) is then added 300 ml of distilled water after which the mixture is dried in an oven at 120° C. for 12 hours. The dried mixture is then calcined by passing air over the mixture at 400° C. for 12 hours. The catalyst thus obtained comprises an interspersed mixture of the oxides of cobalt, aluminum, zinc and molybdenum in the following weight proportions.

| Composition | Weight Percent |
| --- | --- |
| Cobalt oxide | 0.8 |
| Aluminum oxide | 86.2 |
| Zinc oxide | 9.2 |
| Molybdenum oxide | 3.8 |

The alkali metal content, by elemental analysis, is less than 0.1 weight percent of the mixture.

TEST OF THE CATALYST

The reaction system used to evaluate the catalyst is the same as that described in Example 1 using only one reactor containing 10 gms (10 cc) of catalyst at a temperature of 400° C. for 4 hours. The synthesis gas comprising a mixture of hydrogen and carbon monoxide in a volume ratio of 50:50 (molar ratio of hydrogen to carbon monoxide of 1:1).

The test is then repeated using one reactor at 450° C. for 0.5 hour.

The data obtained in the evaluation of the catalyst at 400° C. and 450° C. of this Example 5 are summarized in Table 2.

EXAMPLE 6

PREPARATION OF CATALYST

In this example, the catalyst is prepared by the same procedure and when using the same weights of materials as in Example 5, except that the zinc nitrate is dissolved in 500 ml of distilled water instead of 200 ml as in Example 5. Also, the zinc hydroxide is allowed to settle overnight, the final pH being 7.1. Also, the aluminum nitrate is dissolved in 1500 ml of distilled water instead of 1000 ml as in Example 5. Also, the ammonium hydroxide is added slowly to the aqueous solution of aluminum nitrate at 80° C. instead of room temperature. The dried mixture of zinc hydroxide, aluminum hydroxide and combined precipitate of cobalt and molybdenum is calcined by passing air over the mixture at 300° C. for 12 hours. The catalyst thus obtained comprises an interspersed mixture of the oxides of cobalt, aluminum, zinc and molybdenum in the following weight proportions.

| Composition | Weight Percent |
| --- | --- |
| Cobalt oxide | 0.8 |
| Aluminum oxide | 86.2 |
| Zinc oxide | 9.2 |
| Molybdenum oxide | 3.8 |

The alkali metal content, by elemental analysis, is less than 0.1 weight percent of the mixture.

TEST OF THE CATALYST

The reaction system used to evaluate the catalyst is the same as that described in Example 1 using only one reactor containing 20 gms (25 cc) of catalyst at a temperature of 400° C. for 3 hours. The synthesis gas comprises a mixture of hydrogen and carbon monoxide in a volume ratio of 50:50 (molar ratio of hydrogen to carbon monoxide of 1:1).

The test is repeated using only one reactor at 450° C. for 3 hours.

The data obtained in the evaluation of the catalyst at 400° C. and 450° C. of this Example 6 are summarized in Table 2.

EXAMLE 7

PREPARATION OF CATALYST

In this example, the hydroxides of aluminum and cobalt are coprecipitated and then admixed with the hydroxide of zinc and with ammonium paramolybdate prior to drying according to the procedure which follows.

An aqueous solution of aluminum nitrate and cobaltous nitrate is prepared by dissolving 160.08 gms of aluminum nitrate and 0.616 gm of cobaltous nitrate in 1500 ml of distilled water. Ammonium hydroxide is added slowly to the aqueous solution of aluminum nitrate and cobaltous nitrate at room temperature until the pH of the solution is 6.0. The precipitate thus formed comprising a mixture of aluminum hydroxide and cobaltous hydroxide is separated from the reaction mass by filtration, washed with distilled water and transferred to a 200 ml beaker (I).

An aqueous solution of zinc nitrate is prepared by dissolving 9.138 gms of zinc nitrate in 500 ml of distilled water. The solution is heated to boiling and ammonium hydroxide is added slowly to the aqueous solution of zinc nitrate until the pH of the solution is 7.0. The precipitate thus formed comprising zinc hydroxide is separated from the reaction mass by filtration, washed with 500 ml of distilled water and tranferred to beaker (I) containing the mixed cobaltous hydroxide and aluminum hydroxide. The mixed hydroxides are then further admixed with 4.37 gms of ammonium paramolybdate after which the mixture is dried in air at 400° C. for 12 hours. The catalyst thus obtained comprises an interspersed mixture of the oxides of cobalt, aluminum, zinc and molybdenum in the following weight proportions.

| Composition | Weight Percent |
|---|---|
| Cobalt oxide | 0.4 |
| Aluminum oxide | 75.6 |
| Zinc oxide | 8.6 |
| Molybdenum oxide | 15.2 |

The alkali metal content, by elemental analysis, is less than 0.1 weight percent of the mixture.

TEST OF THE CATALYST

The reaction system used to evaluate the catalyst is the same as that described in Example 1 using only one reactor. The synthesis gas comprises a mixture of hydrogen and carbon monoxide in a volume ratio of 50:50 (molar ratio of hydrogen to carbon monoxide of 1:1).

In starting the test, the synthesis gas at 1000 p.s.i.g. is passed through the system and the flow is stabilized at 18 liters per hour at room conditions. The temperature of the reactor is then increased to 400° C. over a period of about 45 minutes. The reactor is maintained at 400° C. and a pressure of 1000 p.s.i.g. over a period of about 2.5 hours. Gas samples (2 ml) are obtained at room conditions and analyzed by a 2002 Varian Chromatography Unit. At the end of the evaulation, the catalyst is cooled to room temperature and weighed. An observation is made as to whether any liquids are found in the traps.

The data obtained in the evaulation of the catalyst at 400° C. in this Example 7 are summarized in Table 2.

EXAMPLE 8

PREPARATION OF CATALYST AND TEST OF THE CATALYST

The catalyst in this example is the same as that in Example 7. In this example, however, the catalyst is reduced with hydrogen before starting the evaluation. The reaction system used to evaulate the catalyst is the same as that described in Example 1 using only one reactor.

In starting the test, hydrogen is passed through the system at 1000 p.s.i.g. at a flow rate of 18 liters per hour at room conditions. The temperature of the reactor is then increased to 400° C. over a period of about 45 minutes. When a temperature of 400° C. is reached, the hydrogen is passed through the system for only another 10 minutes. Hydrogen is then replaced by synthesis gas comprising a mixture of hydrogen and carbon monoxide in a volume ratio of 50:50 (molar ratio of hydrogen to carbon monoxide of 1:1). The temperature of the reactor is maintained at 400° C. and 1000 p.s.i.g. over a period of 6 hours. Gas samples (2 ml) are obtained at room conditions and analyzed by a 2002 Varian Chromatography Unit as in Example 1. The data obtained in the test are summarized in Table 2.

EXAMPLE 9

PREPARATION OF CATALYST AND TEST OF THE CATALYST

The catalyst in this example is prepared by the same procedure and when using the same weights of materials as in Example 7 except tha zinc nitrate and cobaltous nitrate are mixed and dissolved in 1100 ml of distilled water. Ammonium hydroxide is added slowly at room temperature until the pH of the solution is 9.0.

The catalyst is evaluated in the reaction system of Example 1 wherein the first reactor is maintained at 350° C. and the second reactor is maintained at 400° C.

The data obtained in this Example 9 are summarized in Table 2.

EXAMPLE 10

PREPARATION OF CATALYST AND TEST OF THE CATALYST

In this example, the carbonate of zinc is prepared by reacting zinc nitrate and sodium carbonate. The solution has a pH of 8.0. The hydroxide of aluminum is prepared by reacting aluminum nitrate and ammonium hydroxide. The hydroxide solution has a pH of 6.5. The zinc carbonate and aluminum hydroxide are admixed with a precipitate which is formed by combining an aqueous solution of cobaltous nitrate and an aqueous solution of ammonium paramolybdate which has been neutralized (pH of 6.8) with ammonium hydroxide. The mixture of zinc carbonate, aluminum hydroxide and the precipitate formed from cobaltous nitrate and ammonium paramolybdate is then dried at 120° C. for 12 hours and calcined in the presence of air at 400° C. for 12 hours. The catalyst thus obtained comprises an interspersed mixture of the oxides of cobalt, aluminum, zinc and molybdenum in the following weight proportions.

| Composition | Weight Percent |
|---|---|
| Cobalt oxide | 0.8 |
| Aluminum oxide | 86.2 |
| Zinc oxide | 9.2 |
| Molybdenum oxide | 3.8 |

The alkali metal content, by elemental analysis, is less than 0.1 weight percent of the mixture.

The catalyst is evaluated in the reaction system of Example 1 wherein the first reactor is maintained at 350° C. and the second reactor is maintained at 400° C.

The catalyst is further evaluated in the reaction system of Example 1 using only reactor maintained at 450° C.

The data obtained in this Example 10 are summarized in Table 2.

Table 2

| Ex. No. | Catalyst Composition * | | Catalyst Reduction min/° C. | Reactor Temp. ° C. | S.V. hr$^{-1}$ | CO Conversion % | Final Gas : Vol.% | | | | | | Liquids Water ** | $C_2C_3/C_1$ | Methane Vol.% *** | $C_2$-$C_3$ Vol.% **** |
|---|---|---|---|---|---|---|---|---|---|---|---|---|---|---|---|---|
| | | | | | | | $C_1$ | $C_2$ | $C_3$ | $CO_2$ | $H_2$ | CO | | | | |
| 5 | CoO | 0.8 | None | 400 | 1800 | 13.2 | 3.75 | — | — | 2.5 | 52.5 | 41.25 | — | 0 | 3.8 | 0 |
| | $Al_2O_3$ | 86.2 | None | 450 | 1800 | 27.1 | 5.0 | 1.75 | 0.5 | 6.25 | 42.75 | 43.75 | — | 1.0 | 5.3 | 2.4 |
| | ZnO | 9.2 | | | | | | | | | | | | | | |
| | $MoO_2$ | 3.8 | | | | | | | | | | | | | | |
| 6 | CoO | 0.8 | None | 400 | 1800 | 31.2 | 10 | 0.5 | t | 6.0 | 46 | 37.5 | — | 0.1 | 10.6 | 0.5 |
| | $Al_2O_3$ | 86.2 | None | 450 | 1800 | 48.4 | 12 | 1.0 | 0.5 | 16.0 | 37.5 | 33.0 | — | 0.29 | 14.3 | 1.8 |
| | ZnO | 9.2 | | | | | | | | | | | | | | |
| | $MoO_2$ | 3.8 | | | | | | | | | | | | | | |

Table 2-continued

| Ex. No. | Catalyst Composition* | | Catalyst Reduction min/° C. | Reactor Temp. ° C. | S.V. hr⁻¹ | CO Conversion % | Final Gas : Vol.% | | | | | | Liquids Water** | $C_2C_3 / C_1$ | Methane Vol.%*** | $C_2$-$C_3$ Vol.%**** |
|---|---|---|---|---|---|---|---|---|---|---|---|---|---|---|---|---|
| | | | | | | | $C_1$ | $C_2$ | $C_3$ | $CO_2$ | $H_2$ | $CO$ | | | | |
| 7 | CoO | 0.4 | None | 400 | 1636 | 46.2 | 15 | 1.75 | 0.75 | 13.75 | 32.5 | 36.25 | t | 0.38 | 17.4 | 2.9 |
| | $Al_2O_3$ | 75.7 | | | | | | | | | | | | | | |
| | ZnO | 8.7 | | | | | | | | | | | | | | |
| | $MoO_2$ | 15.2 | | | | | | | | | | | | | | |
| 8 | CoO | 0.4 | 10/400 | 400 | 1636 | 46.8 | 15 | 1.5 | t | 15.0 | 31 | 37.5 | t | 0.22 | 18.8 | 1.7 |
| | $Al_2O_3$ | 75.7 | | | | | | | | | | | | | | |
| | ZnO | 8.7 | | | | | | | | | | | | | | |
| | $MoO_2$ | 15.2 | | | | | | | | | | | | | | |
| 9 | CoO | 0.4 | None | 350/400 | 900 | 58.4 | 21.5 | 2.75 | 0.5 | 20.0 | 20.3 | 35.0 | — | 0.33 | 26.9 | 4.1 |
| | $Al_2O_3$ | 75.7 | | | | | | | | | | | | | | |
| | ZnO | 8.7 | | | | | | | | | | | | | | |
| | $MoO_2$ | 15.2 | | | | | | | | | | | | | | |
| 10 | CoO | 0.8 | None | 350/400 | 818 | 17.9 | 6.5 | t | — | 5.0 | 36 | 52.5 | t | 0.03 | 6.8 | 0 |
| | $Al_2O_3$ | 86.2 | None | 450 | 818 | 49.3 | 18.75 | 1.25 | 0.5 | 15.0 | 25.8 | 38.75 | t | 0.21 | 22.1 | 2.1 |
| | ZnO | 9.2 | | | | | | | | | | | | | | |
| | $MoO_2$ | 3.8 | | | | | | | | | | | | | | |

*Cobalt oxide is presented as cobaltous oxide (CoO) for convenience in providing weight percent values.
 Molybdenum oxide is presented as molybdenum dioxide ($MoO_2$) for convenience in providing weightpercent values.
**t = trace, <1 ml water per 4 cu. ft. of feed gas.
***Volume percent methane in final gas on a carbon dioxide-free basis.
****Volume percent $C_2$-$C_3$ in final gas on a carbon dioxide-free basis.

All of the examples listed in Table 2 report the results obtained when evaluating a catalyst wherein ammonium hydroxide is used to precipitate at least one of the metal oxide precursors selected from cobalt, aluminum and zinc. The data show that higher temperatures, as is also true with the sodium carbonate-precipitated catalysts, result in higher conversions and greater yields of low boiling ($C_1$ to $C_3$) aliphatic hydrocarbons. As is also shown by the data in Table 1, catalysts which have been reduced with hydrogen do not substantially improve the conversion of hydrogen and carbon monoxide to low boiling aliphatic hydrocarbons under the conditions used in the present series of tests.

While my invention has been described above with reference to various specific examples and embodiments, it will be understood that the invention is not limited to such examples and embodiments and may be variously practiced within the scope of the claims hereinafter made.

I claim:

1. A catalyst for use in the synthesis of $C_1$ to $C_3$ aliphatic hydrocarbons from hydrogen and carbon monoxide which consists essentially of an interspersed mixture of cobalt oxide, aluminum oxide, zinc oxide and molybdenum oxide, which mixture by elemental analysis contains less than about 2.0 weight percent of alkali metal, with said catalyst consisting essentially of about 0.2 to about 2.0 weight percent of cotalt oxide, about 55 to about 95 weight percent of aluminum oxide, about 5 to about 15 weight percent of zinc oxide and about 2 to about 20 weight percent of molybdenum oxide.

2. A catalyst composition according to claim 1 wherein the cobalt oxide is from about 0.4 to about 1.0 weight percent of the catalyst, the aluminum oxide is from about 65 to about 90 weight percent of the catalyst, the zinc oxide is from about 7 to about 10 weight percent of the catalyst and the molybdenum oxide is from about 3 to about 16 weight percent of the catalyst, and which mixture, by elemental analysis, contains less than 0.5 weight percent of alkali metal.

3. A catalyst composition according to claim 2 wherein the cobalt oxide is about 0.8 weight percent of the catalyst, the aluminum oxide is about 86.2 weight percent of the catalyst, the zinc oxide is about 9.2 weight percent of the catalyst and the molybdenum oxide is about 3.8 weight percent of the catalyst.

4. A catalyst composition according to claim 2 wherein the cobalt oxide is about 0.4 weight percent of the catalyst, the aluminum oxide is about 75.6 weight percent of the catalyst, the zinc oxide is about 8.6 weight percent of the catalyst and the molybdenum oxide is about 15.2 weight percent of the catalyst.

5. A process for the synthesis of $C_1$ to $C_3$ aliphatic hydrocarbons comprising:

a. contacting hydrogen and carbon monoxide in a volume ratio of about 45:55 to about 60:40 at a temperature of about 350° C. and a pressure of about 200 to about 10,000 p.s.i.g. at a space velocity of about 200 to about 6000 with a catalyst consisting essentially of an interspersed mixture of cobalt oxide, aluminum oxide, zinc oxide and molybdenum oxide, which mixture by elemental analysis contains less than about 0.5 weight percent of alkali metal, said catalyst consisting essentially of about 0.2 to about 2.0 weight percent of cobalt oxide, about 55 to about 95 weight percent of aluminum oxide, about 5 to about 15 weight percent of zinc oxide and about 2 to about 20 weight percent of molybdenum oxide; and b. recovering the $C_1$ to $C_3$ aliphatic hydrocarbon product of said synthesis.

6. A process according to claim 5 wherein the cobalt oxide is from about 0.4 to about 1.0 weight percent of the catalyst, the aluminum oxide is from about 65 to about 90 weight percent of the catalyst, the zinc oxide is from about 7 to about 10 weight percent of the catalyst and the molybdenum oxide is from about 3 to about 16 weight percent of the catalyst, and which mixture by elemental analysis contains less than 0.1 weight percent of alkali metal.

7. A process according to claim 6 wherein the cobalt oxide is about 0.8 weight percent of the catalyst, the aluminum oxide is about 86.2 weight percent of the catalyst, the zinc oxide is about 9.2 weight percent of the catalyst and the molybdenum oxide is about 3.8 weight percent of the catalyst.

8. A process according to claim 6 wherein the cobalt oxide is about 0.4 weight percent of the catalyst, the aluminum oxide is about 75.6 weight percent of the catalyst, the zinc oxide is about 8.6 weight percent of the catalyst and the molybdenum oxide is about 15.2 weight percent of the catalyst.

9. A process for synthesis of $C_1$ to $C_3$ aliphatic hydrocarbons comprising:

a. contacting hydrogen and carbon monoxide in a volume ratio of about 45:55 to about 60:40 at a temperature of about 350° to about 500° C. and a pressure of about 200 to about 10,000 p.s.i.g. at a space velocity of about 200 to about 6000 with a catalyst prepared by (1) precipitating cobaltous hydroxide with ammonium hydroxide from an aqueous solution of cobaltous nitrate at a temperature of about 90° to about 95° C. while maintaining the pH of the solution within the range of about 8.5 to about 9.5; (2) recovering cobaltous hydroxide from "(1)"; (3) precipitating aluminum hydroxide with ammonium hydroxide from an aqueous solution of aluminum nitrate at a temperature of about 20° to about 30° C. while maintaining the pH of the solution within the range of about 6.0 to about 7.5; (4) recovering the aluminum hydroxide from "(3)"; (5) precipitating zinc hydroxide with ammonium hydroxide from an aqueous solution of zinc nitrate at a temperature of about 20° to about 30° C. while maintaining the pH of the solution within the range of about 6.0 to about 7.5; (6) recovering the zinc oxide from "(5)"; (7) admixing the precipitates of cobaltous hydroxide, aluminum hydroxide and zinc hydroxide with an aqueous solution of ammonium paramolybdate; and (8) drying and calcining the mixed hydroxides of cobalt, aluminum and zinc in admixture with the ammonium paramolybdate in the presence of air at a temperature of about 100° to about 400° C. to obtain an interspersed mixture of the oxides of cobalt, aluminum, zinc and molybdenum; and b. recovering the $C_1$ to $C_3$ aliphatic hydrocarbon product of said synthesis.

10. A process for the synthesis of $C_1$ to $C_3$ aliphatic hydrocarbons comprising:

a. contacting hydrogen and carbon monoxide in a volume ratio of about 45:55 to about 60:40 at a temperature of about 350° to about 500° C. and a pressure of about 200 to about 10,000 p.s.i.g. at a space velocity of about 200 to about 6000 with a catalyst prepared (1) precipitating cobaltous hydroxide with ammonium hydroxide from an aqueous solution of cobaltous nitrate at a temperature of about 90° to about 95° C. while maintaining the pH of the solution within the range of about 8.5 to about 9.5; (2) recovering cobaltous hydroxide from "(1)"; (3) precipitating aluminum hydroxide with ammonium hydroxide from an aqueous solution of aluminum nitrate at a temperature of about 20° to about 30° C. while maintaining the pH of the solution within the range of about 6.0 to about 7.5; (4) recovering the aluminum hydroxide from "(3)"; (5) precipitating zinc hydroxide with ammonium hydroxide from an aqueous solution of zinc nitrate at a temperature of about 20° to about 30° C. while maintaining the pH of the solution within the range of about 6.0 to about 7.5; (6) recovering the zinc oxide from "(5)"; (7) admixing the precipitates of cobaltous hydroxide, aluminum hydroxide and zinc hydroxide with an aqueous solution of ammonium paramolybdate; (8) drying and calcining the mixed hydroxides of cobalt, aluminum and zinc in admixture with the ammonium paramolybdate in the presence of air at a temperature of about 100° to about 400° C. to obtain an interspersed mixture of the oxides of cobalt, aluminum, zinc and molybdenum; and (9) preactivating the mixed oxides of cobalt, aluminum, zinc and molybdenum by treating the mixture with hydrogen at a temperature of about 300° to about 450° C. for about 5 minutes to about 48 hours; and b. recovering the $C_1$ to $C_2$ aliphatic hydrocarbon product of said synthesis.

* * * * *

UNITED STATES PATENT OFFICE
CERTIFICATE OF CORRECTION

Patent No. 4039302                    Dated   August 2, 1977

Inventor(s)  Surjit Singh Khera

It is certified that error appears in the above-identified patent and that said Letters Patent are hereby corrected as shown below:

Column 2, line 14, "transistion" should read --transition--;
Column 2, line 22, "catalyst" should read --catalysts--;
Column 4, line 25, "process" should read --processing--;
Column 5, lines 24, 59, and 62, and Column 6, bridging lines 13-14 and bridging lines 39-40, each occurrence, "interspaced" should read --interspersed--; In Table 1, which bridges Columns 13-14, under the table's column headed "Catalyst Composition", the eighth number down from the top instead of "3.3" should read --3.8--, and in the table's one-star footnote, second sentence "inproviding" should show a space between "in" and "providing"; Column 15, line 2, "transformed" should read --transferred-- and bridging lines 52-53, "comprising" should read --comprises--; Column 18, line 9, "tha" should read --that--; In Table 2, which bridges Columns 17-18 and in Table 2-continued, which bridges columns 19-20, in each the table's column headed $\frac{C_2C_3}{C_1}$ should read -- $\frac{C_2C_3}{C_1}$ --; In Table 2, under the table's column headed "CO Conversion", the fourth number down from the top instead of "48.4" should read --48.8--; Column 20, line 33, in Claims 5, "350°C" should read --350° to about 500°C--; and Column 22, line 37, in Claim 10, "$C_2$" should read --$C_3$--.

Signed and Sealed this

Sixth Day of December 1977

[SEAL]

Attest:

RUTH C. MASON
*Attesting Officer*

LUTRELLE F. PARKER
*Acting Commissioner of Patents and Trademarks*